United States Patent [19]

Mynott

[11] Patent Number: 5,824,305
[45] Date of Patent: Oct. 20, 1998

[54] METHOD OF TREATING DISEASES MEDIATED BY CYCLIC NUCLEOTIDE PATHWAYS WITH PURIFIED STEM BROMELAIN PROTEASE

[75] Inventor: Tracey Leahanne Mynott, Middlesex, Great Britain

[73] Assignee: Cortecs (UK) Limited, Great Britain

[21] Appl. No.: 578,701

[22] PCT Filed: Jun. 24, 1994

[86] PCT No.: PCT/GB94/01368

§ 371 Date: Dec. 22, 1995

§ 102(e) Date: Dec. 22, 1995

[87] PCT Pub. No.: WO95/00169

PCT Pub. Date: Jan. 5, 1995

[30] Foreign Application Priority Data

Jun. 25, 1993 [GB] United Kingdom .................. 9313188

[51] Int. Cl.⁶ .............................. A61K 38/46; C12N 9/50
[52] U.S. Cl. ........................ 424/94.65; 435/219; 514/885; 514/886
[58] Field of Search .................. 435/219; 424/94.65; 514/885, 886

[56] References Cited

U.S. PATENT DOCUMENTS 4,197,291  4/1980  Klein et al. ............................ 424/94

FOREIGN PATENT DOCUMENTS 0 358 500 A1  3/1990  European Pat. Off. .
WO 93/01800  2/1993  WIPO .
WO 94/00147  1/1994  WIPO .

OTHER PUBLICATIONS

Desser et al., "Inductions of tumor necrosis factor in human peripheral–blood mononuclear cells by proteolytic enzymes", *Biol. Abstr.*, 91(5):AB–690, Abstr. No. 52552.
Kumakura, et al., "Effect of bromelain on kaolin–induced inflammation in rats", *Biol. Abstr.*, 86(8):AB–895, Abstr. No. 62314.
Batkin et al., "Antimetastatic effect of bromelala with or without its proteolytic and anticoagulant activity", J. Cancer Res. Clin. Oncol. 114(5):507–508 (1988) Abstract.
Ritonja et al., "Stem bromelain: amino acid sequence and implications for weak binding of cystatin", FEBS Lets, 07077, 247(2):419–424 (1989).
Rowan et al., Methods in Enzymology, 244:555–569, 1994.
Kumakura et al., Eur. J. Pharmacol., 150:295–301, 1988.
Taussig et al., J. Ethnopharmacology, 22:191–203, 1988.
Mynott et al., Gastroenterology, 106:A257, Abs., 1994.
Garbin et al., Int. J. Oncology, 5:197–203, 1994.

*Primary Examiner*—David M. Naff
*Assistant Examiner*—Janet M. Kerr
*Attorney, Agent, or Firm*—Pennie & Edmonds LLP

[57] ABSTRACT

The present invention relates to a method of treating various diseases and conditions which are dependent on cyclic nucleotide pathways with purified stem bromelain protease. Administration of isolated and purified stem bromelain protease is effective in the treatment of diseases and conditions including inflammation, atherosclerosis, cancer, and bacterial infections.

3 Claims, 6 Drawing Sheets

FIG. 6 p VALUES REVEAL SIGNIFICANCE AS DETERMINED BY PAIRED T-TEST

FIG. 7 p VALUES REFLECT SIGNIFICANCE AS DETERMINED BY PAIRED T-TEST

FIG. 8 p VALUES REVEALS SIGNIFICANCE AS DETERMINED BY PAIRED T-TEST

FIG. 9 p VALUES REVEAL SIGNIFICANCE AS DETERMINED BY PAIRED T-TEST

METHOD OF TREATING DISEASES MEDIATED BY CYCLIC NUCLEOTIDE PATHWAYS WITH PURIFIED STEM BROMELAIN PROTEASE

BACKGROUND OF THE INVENTION

The present invention relates to the use of one of the components of the enzyme mixture bromelain in the treatment of various conditions which are dependent on cyclic nucleotide and other intracellular and/or extracellular pathways.

Work has already been carried out on the use of proteolytic enzymes in the treatment of infectious and non-infectious diarrhoea in humans and this is described in our co-pending UK applications Nos. 9213862.7 and 9308164.4 from which WO-A-9400147 claims priority. In those applications, various experiments were described which demonstrate that proteolytic enzymes and, in particular, bromelain, are capable of inhibiting secretion. The applications also disclosed that bromelain can reduce toxin binding activity and can inhibit the secretory effect of toxins such as heat labile toxin (LT) and cholera toxin (CT) and also toxins such as heat stable toxin (ST). This is in spite of the fact that ST has a very different mode of action from LT and CT.

LT and ST are both produced by enterotoxigenic strains of *E. coli* (ETEC). Some ETEC strains also produce pilus adhesins called colonisation factor antigens. These adhesins promote attachment of ETEC strains to the small intestinal mucosa, thereby facilitating colonisation and delivery of enterotoxin. Diarrhoeal disease is ultimately dependent on production and efficient delivery of enterotoxin.

The enterotoxins stimulate secretion by cells by activation of signal pathways. Internal signals within cells are carried by "second messengers". At least three signal pathways are known to be important for secretion. One pathway employs the second messenger cyclic adenosine monophosphate (cyclic AMP). Another employs the second messenger cyclic guanosine monophosphate (cyclic GMP). These two messengers are referred to as cyclic nucleotides. The third signal pathway ($Ca^{2+}$-dependent pathway) requires $Ca^{2+}$ as the second messenger.

The mode of action of LT is virtually identical to that of cholera toxin (CT), which has been well documented. Briefly, the B promoter binds to a ganglioside receptor GM1 [galactosyl-N-acetylgalactosaminyl-(N-acetyl-neuraminyl) galactosylglucosylceramide] located on the brush border membrane. Recent studies have shown that LT also binds to a structurally related glycoprotein to which CT does not bind. Binding is followed by translocation of the A subunit through the membrane and release of the A1 fragment into the cytosol after proteolytic activation. Adenylate cyclase activity is stimulated following catalysing the NAD-dependent cyclase complex. As a result, adenylate cyclase is locked into an active form through inhibition of an inherent feedback regulatory mechanism which normally involves the hydrolysis of GTP to GDP and phosphate (Pi). Inactivation of the regulatory subunit leads to increased levels of the second messenger, cyclic AMP (cAMP). cAMP activates an enzyme called protein kinase A which, in turn, phosphorylates proteins. The phosphorylation of proteins (that is, the addition of a phosphate group) results in the opening of chloride channels and therefore secretion. Increased levels of cAMP are also known to inhibit the absorption of NaCl.

The mode of action of ST is less well understood than that of LT. STs produced by ETEC are a heterogeneous group of molecules having a molecular weight of from about 2000 to 5000 Da and which are non-antigenic in their native state. An example of a common ST is ST I which can be either an 18 or a 19 amino acid peptide. In contrast to LT, which activates adenylate cyclase of intestinal cells, ST I stimulates only the particulate form of intestinal guanylate cyclase. The action of ST I is almost instantaneous. The initial step in the biological action of ST is its interaction with membrane-bound guanylate cyclase in the cells, leading to an increase in the intracellular concentration of cyclic GMP followed by activation of cyclic GMP-dependent protein kinase (protein kinase G). This culminates in the inhibition of $Na^+$ absorption and stimulation of $Cl^-$ secretion. ST-induced fluid secretion is relatively short-lived and is readily reversed, in contrast to the delayed but sustained and irreversible effects of LT on adenylate cyclase and fluid secretion. The intestinal ST I receptor has been shown to have guanyl cyclase activity although other proteins or glycoproteins may also have a role.

Intestinal transcellular absorption and secretion of electrolytes is driven by the $Na^+/K^+$ ATPase pump, located in the enterocyte basolateral membrane. Water flows passively with electrolytes in response to osmotic gradients, and $Na^+$ and $Cl^-$ are the predominant ions involved in the absorption and secretion of water. The absorptive and secretory processes in the small intestine are separated. In general, electrolytes and water are secreted from crypt enterocytes, and reabsorption takes place through villus enterocytes. Normally, secretion and absorption are balanced to prevent dehydration. The diarrhoeal response caused by LT and CT results from stimulation of a cAMP-mediated active secretory mechanism (i.e. the cAMP pathway). The diarrhoeal response caused by ST is from stimulation of the cGMP pathway. cAMP and cGMP exert an anti-absorptive effect on villus cells by inhibiting uptake of NaCl, and in addition stimulates active chloride secretion by crypt cells (by opening of the chloride channels). When the level of secretion increases beyond the ability of the colon to reabsorb water and electrolytes lost from the small intestine, diarrhoea results that can lead to severe dehydration and, eventually in extreme cases, death.

If subjects are adequately rehydrated after infection, by CT, LT or ST, examination of the intestinal mucosa shows no bacterial invasion, no infiltration of leukocytes, and no capillary damage, even at the ultrastructural level. Consistent with the normal morphology, absorptive processes for nutrients do not seem to be impaired.

Experiments which led to the making of this invention have shown, by the use of an ex vivo rabbit intestinal tissue model in Ussing chambers, that bromelain and similarly acting enzymes significantly inhibited the secretory effect of LT, CT and also ST; more specifically, bromelain completely inhibited the net anion flux of $Cl^-$, and hence the secretagogue effect of toxins such as LT and CT and also ST. The proposed mechanism of action of bromelain is that it prevents attachment of toxin by modification of the toxin receptors located on the brush border membrane. It is also hypothesised that bromelain has an additional mechanism for inhibiting fluid secretion since it appears to inhibit secretion induced by prostaglandin $E_2$ and by other secretagogues that do not interact with cellular receptors, namely theophylline, 8-Br-cGMP, 8-Br-cAMP and Ca-ionophore.

The work described demonstrates that bromelain appears to have an effect on cyclic nucleotide pathways and it is for this reason that it is successful in treating and preventing diarrhoea which is caused by either the LT or the ST type mechanism.

It therefore follows that bromelain would also be likely to be useful in the treatment or prophylaxis of diseases other than diarrhoea which are mediated by cyclic nucleotides. Examples of such diseases include cancer, inflammation (bromelain has been found to have non-steroidal anti-inflammatory action), atherosclerosis and bacterial infections such as cholera, diphtheria and pertussis.

Bromelain has already been found to be useful in the treatment of some such conditions but there has been no rationale suggested for the variety of uses to which bromelain has been put. It would seem that the action of bromelain on cyclic nucleotide pathways could provide an explanation for the wide variety of diseases and conditions in which bromelain has already been found to be useful.

Bromelain is the collective name for the proteolytic enzymes found in the tissues of the plant Bromeliaceae. Bromelain is a mixture of various moieties derived from the stem of the pineapple (*Ananas comosus*). It contains at least two proteolytic enzymes but also non-proteolytic enzymes, including an acid phosphatase and a peroxidase; it may also contain amylase and cellulase activity. In addition, various other components are also present.

There are various problems associated with the use of a mixture of components as a pharmaceutical agent and these include the fact that one or other of the components may produce unwanted side effects without giving benefit to the patient. This problem could be solved if a single component of the mixture could be found which is responsible for the activity of bromelain on cyclic nucleotide pathways. In addition, if a single component could be found, the amount of drug substance administered to a patient could be reduced since it would be possible to administer only the active portion of the bromelain mixture.

SUMMARY OF THE INVENTION

The present inventors have now discovered that the component of the bromelain mixture which appears to be responsible for its action on cyclic nucleotide pathways is an enzyme known as stem bromelain protease. This enzyme has been previously described but no use has been ascribed to it.

Stem bromelain protease has been described by Ritonja et al (*FEBS Letters,* 247, 419–424 (1989)) and has the amino acid sequence set out below (SEQ ID NO 1):

| Ala 1 | Val | Pro | Gln | Ser 5 | Ile | Asp | Trp | Arg | Asp 10 | Tyr | Gly | Ala | Val | Thr 15 | Ser |
| Val | Lys | Asn | Gln 20 | Asn | Pro | Cys | Gly | Ala 25 | Cys | Trp | Ala | Phe | Ala 30 | Ala | Ile |
| Ala | Thr | Val 35 | Glu | Ser | Ile | Tyr | Lys 40 | Ile | Lys | Lys | Gly | Ile 45 | Leu | Glu | Pro |
| Leu | Ser 50 | Glu | Gln | Gln | Val | Leu 55 | Asp | Cys | Ala | Lys | Gly 60 | Tyr | Gly | Cys | Lys |
| Gly 65 | Gly | Trp | Glu | Phe | Arg 70 | Ala | Phe | Glu | Phe | Ile 75 | Ile | Ser | Asn | Lys | Gly 80 |
| Val | Ala | Ser | Gly | Ala 85 | Ile | Tyr | Pro | Tyr | Lys 90 | Ala | Ala | Lys | Gly | Thr 95 | Cys |
| Lys | Thr | Asp | Gly 100 | Val | Pro | Asn | Ser | Ala 105 | Tyr | Ile | Thr | Gly | Tyr 110 | Ala | Arg |
| Val | Pro | Arg 115 | Asn | Asn | Glu | Ser | Ser 120 | Met | Met | Tyr | Ala | Val 125 | Ser | Lys | Gln |
| Pro | Ile 130 | Thr | Val | Ala | Val | Ala 135 | Asp | Ala | Asn | Ala | Asn 140 | Phe | Gln | Tyr | Tyr |
| Lys 145 | Ser | Gly | Val | Phe | Asn 150 | Gly | Pro | Cys | Gly | Thr 155 | Ser | Leu | Asn | His | Ala 160 |
| Val | Thr | Ala | Ile | Gly 165 | Tyr | Gly | Gln | Asp | Ser 170 | Ile | Ile | Tyr | Pro | Lys 175 | Lys |
| Trp | Gly | Ala | Lys 180 | Trp | Gly | Glu | Ala | Gly 185 | Tyr | Ile | Arg | Met | Ala 190 | Arg | Asp |
| Val | Ser | Ser 195 | Ser | Ser | Gly | Ile | Cys 200 | Gly | Ile | Ala | Ile | Asp 205 | Pro | Leu | Tyr |
| Pro | Thr 210 | Leu | Glu | Glu | | | | | | | | | | | |

Therefore in a first aspect of the invention, there is provided isolated and purified stem bromelain protease having the sequence of SEQ ID NO 1 or a sequence substantially homologous thereto for use in medicine except for the treatment of diarrhoea.

The term "substantially homologous" would be well understood by one skilled in the art who would easily be able to determine whether or not two sequences were substantially homologous. However, in general, amino acid sequences can be described as substantially homologous when they have at least 40% homology although, for the purpose of the present invention, it is preferable for a sequence to have at least 50%, 60%, 70%, 80%, 90% or 95% homology to the amino acid sequence of SEQ ID NO 1. In addition, the residues which are compared need not be in exactly the same positions in two sequences which are substantially homologous but rather, one of the sequences may have various inserted or deleted amino acid residues or regions with respect to the sequence with which it is compared.

The use of stem bromelain protease in the treatment of diarrhoea is disclosed in WO-A-9400147 and the disclosure has the same priority date as the present application.

In discovering that stem bromelain protease is the active component of bromelain, the present inventors have made possible the administration of the active component of bromelain to patients who may have adverse reactions to other components of the mixture. In addition, smaller quantities of a composition can be used while still ensuring that a patient receives an effective dose of the active compound.

In addition to its action on cyclic nucleotide pathways, data indicate that stem bromelain protease can also inhibit secretion by factors which do not require cyclic nucleotides. For example, it seems possible that it may also inhibit secretion by operating on the calcium dependent pathways. It is therefore possible that stem bromelain protease may act, not on the different cyclic nucleotide pathways themselves but at the final step of the pathways which may be at the cell surface.

In addition, there is also some evidence that stem bromelain protease may enhance absorption of secreted fluid and nutrients as well as inhibiting secretion.

In another experimental model, the effect of bromelain treatment on other physiologically important receptor was tested. The influx of the amino acids, glutamic acid, lysine and leucine and of the dipeptide, glycine-phenylalanine was investigated.

Results from the influx studies revealed that there was no interference with glucose, amino acid and dipeptide influx, supporting that bromelain has no adverse effect on receptors important for nutrient uptake. In fact, bromelain appeared to increase the absorption of these nutrients.

One theory which may explain the activity of stem bromelain protease is that it may have some effect on the chloride or other channels either to prevent the channels from opening or to block them. Either of these actions would account for the action of stem bromelain protease on cyclic nucleotide pathways but it should be stressed that the efficacy of stem bromelain protease in the treatment of diseases and conditions mediated by cyclic nucleotides is not dependent on the accuracy of this proposal. If stem bromelain protease does, indeed, block chloride or other channels, then this would indicate that the effect is not intracellular.

However, the significant point about these observations is that stem bromelain protease will affect any disease or condition mediated by cyclic nucleotides.

Isolated and purified stem bromelain protease may therefore be of use in a method for the treatment or prophylaxis of diseases or conditions mediated by cyclic nucleotide pathways, the method comprising administering to a patient an effective amount of stem bromelain protease.

In a second aspect of the invention there is provided the use of isolated and purified stem bromelain protease in the preparation of an agent for the treatment or prophylaxis of diseases or conditions mediated by cyclic nucleotides other than diarrhoea.

The invention may be effective in addressing diseases or conditions caused by organisms that elicit a response by opening of chloride channels or other channels. Moreover, stem bromelain protease would be expected to be effective against any agent being infectious or non-infectious that mediates secretion by activating signal pathways, ie by either the cAMP, cGMP or calcium-dependent pathway. Examples of diseases or conditions which may be treatable include cancer, inflammation (bromelain has been found to have non-steroidal anti-inflammatory action), atherosclerosis and bacterial infections such as cholera, diphtheria and pertussis.

Stem bromelain protease may be administered by a variety of routes including enteral, for example oral, nasal, buccal, or anal administration or parenteral administration for example by intravenous or intramuscular injection. The oral route is, however, preferred.

Therefore, in a third aspect of the invention there is provided a pharmaceutical composition comprising isolated stem bromelain protease together with a pharmaceutically acceptable excipient or carrier.

To assist survival of the stem bromelain protease through the stomach when administered orally, it may be desirable to formulate the enzyme in an enteric-protected preparation. Other orally administrable formulations include syrups, elixirs, and hard and soft gelatin capsules, which may also be enteric-coated.

Bromelain activity is stable over a wide pH range (pH 2–9). Therefore, it may not be necessary to enteric-protect (or enteric-coat) the stem bromelain protease from the acid conditions in the stomach. It may, however, be necessary to protect the enzyme from digestion by acid proteases in the gut. Stem bromelain protease may therefore, be administered with a buffering agent, for example bicarbonate.

The preferred delivery system would be controlled release of the enzyme, to ensure complete removal of receptor sites along the intestine and/or exposure of all enterocytes to the protease. It would be desirable to have a combination of protection (to prevent digestion and absorption) and release all the way to the ileum.

Dosage of bromelain is conventionally measured in Rorer units, FIP units, BTU (bromelain tyrosine units), CDU (casein digestion units), GDU (gelatin digestion units) or MCU (milk clotting units). One Rorer unit of protease activity is defined as that amount of enzyme which hydrolyses a standardisation casein substrate at pH 7 and 25° C. so as to cause an increase in absorbence of 0.00001 per minute at 280 nm. One FIP unit of bromelain activity is contained in that amount of a standard preparation, which hydrolyses a suitable preparation of casein (FIP controlled) under the standard conditions at an initial rate such that there is liberated per minute an amount of peptide, not precipitated by a specified protein precipitation reagent, which gives the same absorbence as 1 $\mu$mol of tyrosine at 275 nm. BTUs, CDUs, GDUs and MCUs are as defined in the literature, as follows:

BTU

One bromelain tyrosine unit is that amount of enzyme which will liberate one micromole of tyrosine per minute under the conditions of the assay (for example, after digestion of an acid denatured haemoglobin substrate at pH 5 and 30° C.).

CDU

That amount of enzyme which will liberate one microgram of tyrosine after one minute digestion at 37° C. from a standard casein substrate at pH 7.0.

GDU

The enzyme activity which liberates one milligram ($10^{-3}$ g) of amino nitrogen from a standard gelatin solution after 20 minutes digestion at 45° C. and at pH 4.5.

1100 BTU/g=750 CDU/mg=1200 GDU/g.

While the precise dosage will be under the control of the physician or clinician, it may be found that daily dosages of from 50 to 4000 GDU/day is appropriate, for example from 100 to 1000 GDU/day. The daily dose may be given in one or more aliquots per day, for example twice, three times or four times a day.

BRIEF DESCRIPTION OF THE DRAWINGS

The invention will now be described by the following examples. The examples refer to the accompanying drawings, in which.

DETAILED DESCRIPTION OF THE INVENTION

Example 1: Investigation of Pre-treatment of Mucosal Tissue with Protease on LT Action in Ussing Chambers The use of rabbit intestinal tissue mounted in Ussing chambers (Ussing and Zerahn *Acta. Phys. Scandinav.* 23 110–127 (1951)) is a classical technique for studying the process of transport across intestinal tissue. The use of this ex vivo model has also proven invaluable for the study of the mechanisms of action of enterotoxins. Solutions containing CT or LT when added to the mucosal side of mounted tissue, elicit a secretory response from cells similar to that observed with perfusion of CT or LT in rabbit ileum in vivo. Addition of toxin results in an increase in transepithelial electrical potential difference (PD) and short circuit current ($I_{SC}$) of ileal mucosa by stimulation of a net anion secretory flux. This results in the serosal side becoming more positive relative to the lumenal side. The net flux of negative charge can be monitored electrochemically by means of an electrical apparatus comprising matched reference electrodes connected to a high impedance potentiometer.

Because of the usefulness of the Ussing chamber model in monitoring toxin action, the effectiveness of many antidiarrhoeal drugs in reversing the secretory action of toxins have been tested. This example relates to experiments designed to observe the use of protease in inhibiting LT toxin secretory activity. Concurrently, the effect on the glucose-$Na^+$ active co-transport function is monitored as an indicator of tissue viability.

Experiments were performed according to Field et al, (*Am. J. Physiol.* 220 1388–1396 (1971)) with modifications described by Fasano et al, (*Proc. Natl. Acad. Sci. USA* 88 5242–5246 (1991)). Adult male New Zealand White rabbits (2–3 kg) were anaesthetised by methoxyflurane inhalation and then sacrificed by air embolism. A 15 cm segment of distal ileum was quickly excised and cut open along the mesenteric border. The ileum was then rinsed clean of luminal contents and stripped of muscular and serosal layers by means of blunt dissection. The active transport processes of the mucosa have been reported to be better maintained in stripped as opposed to unstripped ileum (Field et al, 1971 loc cit). The resulting preparation consisted of epithelium, lamina propria and muscularis mucosae. Four sections of mucosa were prepared as such from the one animal, and mounted in Lucite Ussing chambers of aperture 1.12 $cm^2$. Each surface of the tissue was continually bathed (10 ml per surface) in freshly prepared Ringers buffer containing NaCl (53 mM), KCl (5 mM), $Na_2SO_4$ (30.5 mM), mannitol (30.5 mM), $Na_2HPO_4$ (1.69 mM), $NaH_2PO_4$ (0.3 mM), $CaCl_2$ (1.25 mM), $MgCl_2$ (1.1 mM) and $NaHCO_3$ (25 mM). The bathing solution was maintained at 37° C. with water-jacketed reservoirs connected to a constant-temperature circulating pump and gassed with 95% $O_2$/5% $CO_2$.

The PD (the difference in voltage measured on the mucosal side versus the serosal side of the tissue) and $I_{SC}$ (the amount of current needed to nullify the PD) were then measured as previously described (Field et al, 1971 loc cit). A positive PD indicated that the serosal potential was higher than the luminal potential, that is the net flux from the mucosa (M) to serosa (S) was positive. The tissue resistance (R) for each animal was also calculated from Ohm's Law where $I_{SC}$=PD/R, so that results between individual animals could be compared. Prior to mounting the tissue, the fluid resistance ($R_f$) was determined and incorporated into the calculations. Once the tissue was mounted and prior to experimentation, the $I_{SC}$ was determined at approximately 10 min. intervals until the tissue reached a steady state. Four sections of tissue from the same animal were mounted simultaneously and used for each experiment. To test for leakiness of the system owing to perforations of the ileal tissue, 200 µl of 0.5 mM solution of glucose and mannitol diluted in Ringers was added to the serosal and mucosal side respectively prior to experimentation.

Once the tissue reached equilibrium (time 0), the test material (0–100 µl) was added to the mucosal side. The same volume of sample was added to the serosal side to preserve osmotic balance. Variations in $I_{SC}$, PD and R were then recorded every 5–10 mins. At the end of every experiment, 200 μl of 0.5M glucose was added to the mucosal side of each chamber. Only those tissues that showed an increase in $I_{SC}$ in response to glucose (indicating tissue viability) were included in the analysis. The increase in $I_{SC}$ upon glucose addition is due to enhancement of $Na^+$ absorption mediated by the electrogenic coupled transfer of $Na^+$ with glucose into the cell.

Pieces of rabbit ileum exposed to a range of concentrations of bromelain (0–1000 μg/ml) for 30 min were examined by light microscopy and electron microscopy. Tissue exposed to PBS alone was used for comparison.

For light microscopy, tissue was fixed in neutral buffered formalin and stained with haematoxylin/eosin and tissue gram stain. Tissues for electron microscopy were fixed in 3% (v/v) glutaraldehyde/0.1M sodium cacodylate buffer (pH 7.4) and then stored at 4° C. until required.

1a Light Microscopy

At examination of the tissues, particular attention was directed to morphological and structural changes in both the intestinal villi and the brush border lining.

Tissue samples exposed to 1000 μg/ml of bromelain did not respond to glucose addition at the end of the treatment period, indicating that the tissue was no longer viable. Light microscopic examination of these samples revealed pronounced marked vacuolar degeneration. The villus structure was absent and there was coagulation necrosis of individual epithelial cells lining the remnants of the villus.

The ileal tissue that was treated with 50 μg/ml of bromelain was viable after glucose addition; however, the $I_{SC}$ response was not maximal, indicating some necrosis of the tissue. Light microscopy confirmed this observation, whereby samples exhibited some coagulation necrosis of luminal epithelial cells and vacuolar degeneration, indicating dead or dying cells. The villus architecture of these tissue preparations, however, remained intact.

Tissue treated with 10 μg/ml of bromelain had an intact mucosa with villi lined by tall columnar epithelium. In general the tissue appeared normal, yet occasional cells showed some coagulation necrosis. There was a large response to glucose addition after 30 minutes of bromelain treatment, indicating healthy, viable tissue. The occasional cells that may have been affected by bromelain treatment, therefore did not appear adversely to affect the absorptive capacity of the tissue.

1b Electron Microscopy

Examination of tissue treated with 10 μg/ml of bromelain by transmission electron microscopy revealed no morphological changes to the microvilli. The glycocalyx or mucus overlay was seen to be intact.

Figure 1:
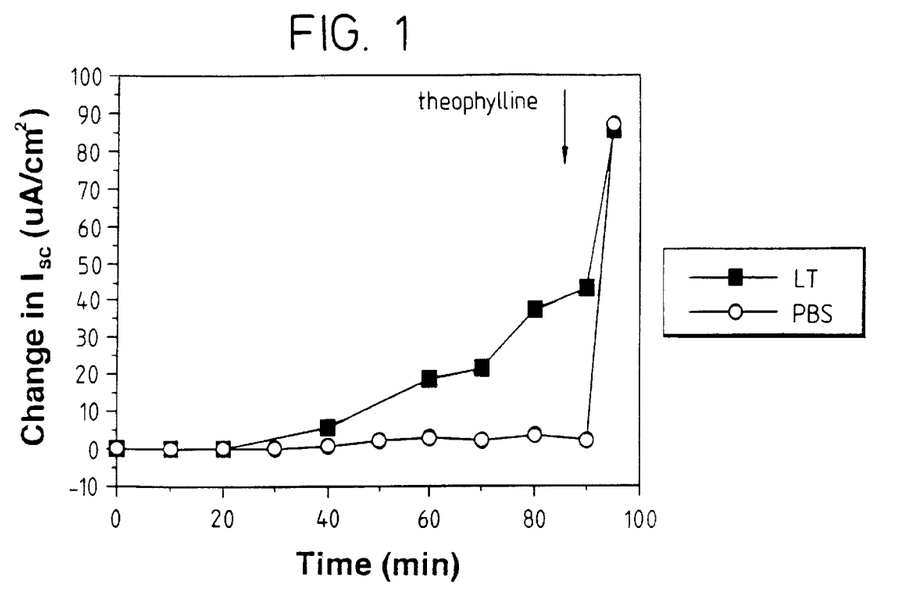
FIG. 1 shows the effect of pure LT on rabbit ileal $I_{SC}$. Symbols represent the mean values at each time point for 4 animals. LT (2.5 µg/ml) or PBS (15 µl) was added to the mucosal bathing solution at time 0. The arrow indicates time at which 5 mM theophylline was added to serosal bathing solution.

1c Effect of LT on $I_{SC}$ Across Ileal Mucosa

The changes in $I_{SC}$ produced by addition of 25 μg of pure LT (final concentration was 2.5 μg/ml) to the luminal side of the ileal mucosa are shown in FIG. 1. the $I_{SC}$ began to increase 40–50 min after addition of toxin. In chambers where tissue was exposed to PBS only, there was a negligible change in $I_{SC}$. Studies have shown that 40–60 min after CT addition there is a gradual progression to a maximal effect which occurred over the next few hours. Continuation of this effect occurred despite removal of all free toxin. Toxin that had been heat treated prior to exposure to the tissue had no effect. In addition, toxin exposed to the serosal side of the tissue had no effect on $I_{SC}$ indicating that action only occurred after binding to receptors located on the brush border membrane.

Theophylline, a methylxanthine, was added to the serosal side of the tissue to observe the change in $I_{SC}$ due to cAMP. Theophylline inhibits cyclic nucleotide phosphodiesterases and thus elevates cAMP by inhibiting the conversion of AMP to 5'-AMP. The effects of theophylline, cAMP alone and saturable amounts of CT on Na and Cl fluxes are the same. The effects of theophylline on flux, however, occur after only a few minutes.

Addition of theophylline (final concentration 5 mM) to the serosal side of the toxin-treated tissue resulted in a further increase in $I_{SC}$. The increase in $I_{SC}$ due to theophylline on PBS treated mucosa was equivalent to the final $I_{SC}$ due to the combined toxin and theophylline treatment. This indicates that the change in $I_{SC}$ due to LT addition was due to the toxin action on cAMP and not by any other mechanism. The same change in $I_{SC}$ also showed that the amount of toxin and hence its activity used in this experiment was not maximal. That is, more toxin was required to occupy all receptors in order to exhibit maximal levels of cAMP and hence $I_{SC}$.

At the completion of the experiment, glucose was added to the lumenal side of the chamber. This resulted in a further increase in $I_{SC}$ indicating that the tissue was viable.

1d Effect of Bromelain on Secretory Effect caused by *Escherichia coli* heat-labile Toxin (LT)

Bromelain diluted in PBS (final concentration 10 μg/ml) was added to both the mucosal and serosal side of the tissue. Control chambers were included whereby bromelain (100 μg/10 μl) was first pre-incubated (30 min at 37° C.) with an equal volume of an anti-bromelain antibody (IgG) (0.5 mg/ml) prior to addition to the chamber. Other chambers contained antibody or PBS alone. All chambers were then allowed to incubate for 30 min to enable sufficient bromelain pre-treatment of the mucosal tissue. Prior to addition of toxin the chambers were completely emptied of Ringers (see above) and rinsed twice to ensure complete removal of antibody and bromelain. The chambers were then re-filled with fresh Ringers and the tissue allowed to stabilise. LT (2.5 μg/ml) was then added to the mucosal side and the experiment completed as described above.

Figure 2:
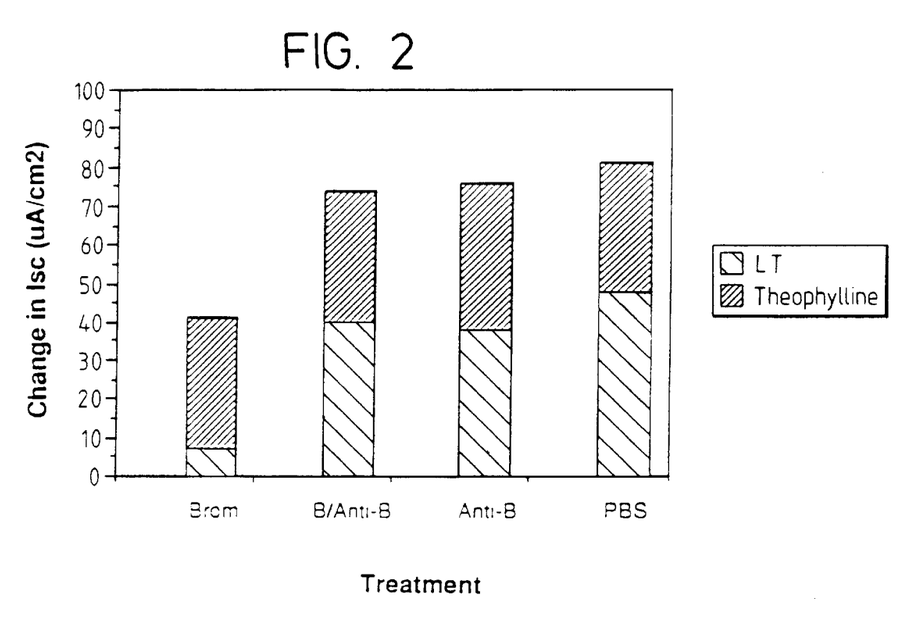
FIG. 2 shows the effect of bromelain on ileal $I_{SC}$. Columns represent the mean values 90–100 min after LT (2.5 µg/ml) addition, and 5 min after theophylline (5 mM) addition. Ileal tissue from 4 animals were pre-treated with bromelain (brom) for 30 minutes prior to toxin addition. Control chambers were pre-treated with bromelain plus antibody (B/Anti-B), antibody (Anti-B) or PBS alone.

FIG. 2 shows the change in $I_{SC}$ produced by pre-treatment of tissue with bromelain or control substance prior to addition of LT. In all control chambers, the $I_{SC}$ began to increase 40–50 min after addition of toxin as observed above. This result indicates that the anti-bromelain IgG and bromelain pre-incubated with antibody had no effect on the LT action. It also shows that changing the Ringers buffer had no effect on the tissue.

In chambers that were pre-treated with bromelain, there was no change in $I_{SC}$ after 60 min, indicating that the bromelain had completely inhibited the secretory effect of LT. Addition of theophylline to control chambers, showed a further increase in $I_{SC}$ of 40% to 50%. In comparison, addition of theophylline to the bromelain treated chamber only showed a similar increase in $I_{SC}$. The final change in $I_{SC}$ was therefore 40% to 50% less than that of the combined effect of LT and theophylline in control chambers. It is presumed that some other mechanism of action of bromelain in inhibiting fluid secretion may be present. Bromelain has been reported to inhibit the synthesis of prostaglandins, which are known to inhibit cAMP production (Taussig and Batkin, 1988). Other molecules that inhibit the synthesis of prostaglandins, including aspirin, indomethacin and ibuprofen, have also been shown to inhibit intestinal fluid secretion induced by bacterial toxins (Gots et al, 1974; Finch and Katz, 1972; Peterson et al, 1988).

These data indicate that the bromelain had completely inhibited the net anion flux of $Cl^-$ and hence secretagogue effect of LT. The data also indicate that bromelain has an additional mechanism for inhibiting fluid secretion, other than its ability to inhibit binding of toxin to intestinal receptors. The observation that total $I_{SC}$ levels in bromelain-treated tissue combined with prostaglandin (see Example 2b) or theophylline failed to reach the same levels as control tissues, supports this hypothesis.

Addition of glucose at the end of the experiment showed a further increase in $I_{SC}$, therefore indicating that glucose-$Na^+$ transport was unaffected. Because the enhancement of Na absorption did not appear to be substantially effected by pre-treatment of tissue with protease, the implication is that bromelain does not result in extensive physiological damage to the mucosa.

This result is confirmed by the light microscopy study, referred to above and by influx studies described in Example 7b.

Example 2: Investigation of Pre-treatment of Mucosal Tissue with Protease on CT Action in Ussing Chambers 2a Effect of bromelain on secretory effect caused by cholera toxin (CT).

In a similar experiment to that described in Example 1d, bromelain diluted in PBS (final concentration 15 ug/ml) was added to both the mucosal and serosal side of the ileal tissue. Control tissues were treated with PBS alone. Chambers were allowed to incubate for 30 minutes and rinsed as described above. CT (10 ug) was then added to the mucosal side and the experiment completed as before.

Figure 3:
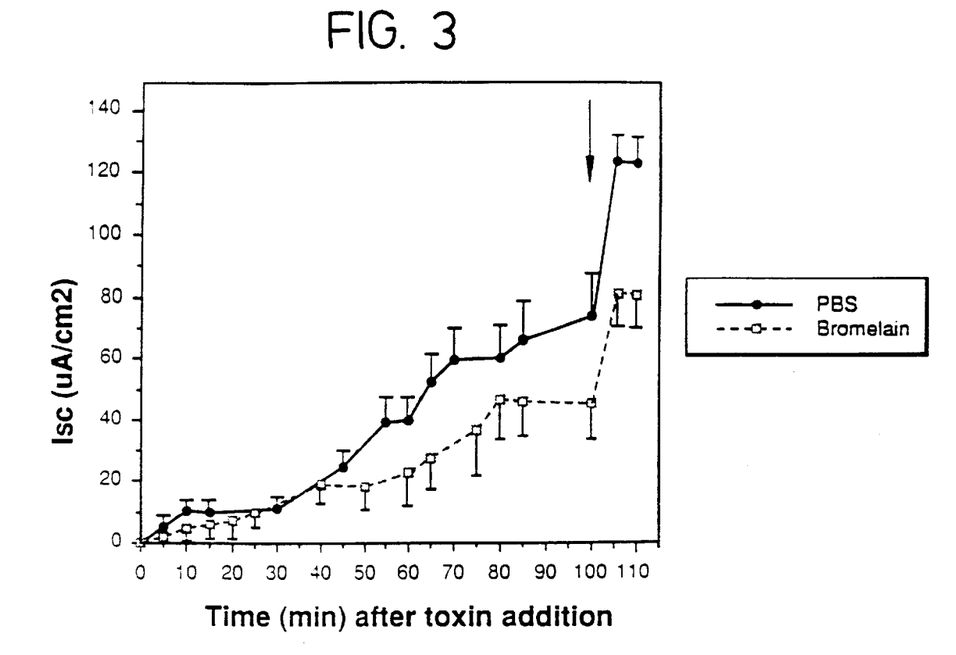
FIG. 3 shows the effect of pre-treatment of ileal tissue with PBS or bromelain (15 ug/ml) on $I_{SC}$. CT (1 ug/ml) was added to the mucosal bathing solution at time 0. Number of animals tested was 9. Symbols with bars represent the mean ±SE for 9 animals at selected time points. The arrow indicates the time at which 5 mM theophylline was added to the serosal bathing solution after $I_{SC}$ values reached a plateau.

FIG. 3 shows the change in $I_{SC}$ produced by pre-treatment of tissue with PBS or bromelain. The data shows that bromelain reduced the change in $I_{SC}$ and PD and therefore the secretory effect caused by CT. The reduction in $I_{SC}$ and PD values induced by bromelain was 60% (p=0.001) and 70% (p=0.002) respectively. See Table 1 of Ussing chamber data.

levels of cAMP as a result of reduced prostaglandin levels, exogenous prostaglandin was added to the serosal side of the chamber when $I_{SC}$ and PD values had reached a plateau. PE2 ($1 \times 10^5 M$) was added instead of theophylline. The data presented in Table 1 of Ussing chamber data, indicate that there is still a reduction of 48% and 64% respectively, in the total $I_{SC}$ and PD in bromelain and CT treated tissue, compared with the combined effect of CT and PE2 in control (PBS treated) chambers.

These data suggest the additional mechanism by which bromelain reduces fluid secretion cannot be completely explained by its reported ability to inhibit the synthesis of prostaglandins.

Example 3: Effect of Bromelain on Secretory Effect Due to *Escherichia Coli* Heat Stable Toxin (ST)

Experiments were conducted in a similar manner as for those using LT (Example 1d) and CT (Example 2a). Bromelain diluted in PBS (final concentration 15 μg/ml) was added to both the mucosal and serosal side of the ileal tissue. Control tissues were treated with PBS alone. Chambers were allowed to incubate for 30 minutes and rinsed as described above. ST (300 units) was then added to the mucosal side and the experiment completed as before.

Figure 4:
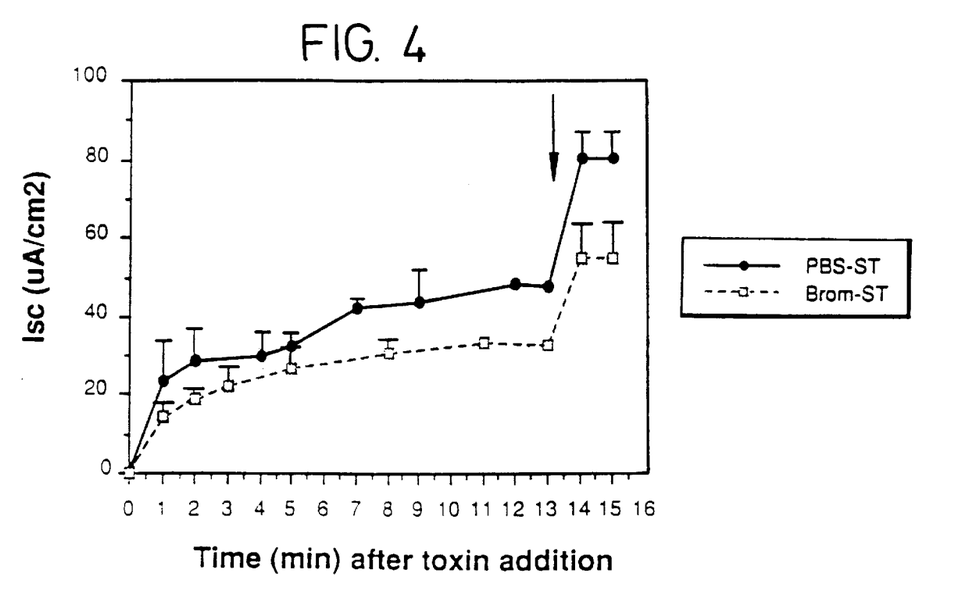
FIG. 4 shows the effect of pre-treatment of ileal tissue with PBS or bromelain (15 ug/ml) on $I_{SC}$. ST (300 units) was added to the mucosal bathing solution at time 0. Number of animals tested was 6. Symbols with bars represent the mean +SE at selected time points. The arrow indicates the time at which 0.2 mM 8 bromo cGMP was added to the serosal bathing solution after $I_{SC}$ values reached a plateau.

FIG. 4 shows the change in $I_{SC}$ produced by pre-treatment of tissue with PBS or bromelain. The data show that bromelain reduced the change in $I_{SC}$ and PD and therefore the secretory effect caused by ST. The reduction in $I_{SC}$ and PD values induced by bromelain was 34% (p=0.0313) and 33% (p=0.06) respectively and this is shown in Table 1.

8-Bromoguanosine 3' 5'-cyclic monophosphate (final concentration 0.2 mM), an analogue of cGMP known to simulate cGMP production, was added to the serosal side of the tissue when PD and $I_{SC}$ values had reached a plateau

TABLE 1

Effect of bromelain treatment of ileal tissue on Δ $I_{sc}$ and PD

| Toxin | n | Δ $I_{sc}$ (μA/cm²) | | | Δ PD (mV) | | |
|---|---|---|---|---|---|---|---|
| | | PBS | Bromelain | P | PBS | Bromelain | P |
| LT | 7 | 52.0 ± 7.3 | 13.4 ± 5.2 | 0.02 | 1.1 ± 0.2 | 0.3 ± 0.2 | 0.03 |
| +theo | 7 | 90.6 ± 10.2 | 45.8 ± 8.5 | 0.03 | 2.2 ± 0.3 | 1.0 ± 0.3 | 0.01 |
| CT | 9 | 58.5 ± 8.3 | 25.7 ± 6.9 | 0.001 | 1.2 ± 0.1 | 0.4 ± 0.2 | 0.002 |
| +theo | 6 | 107.4 ± 15.0 | 62.5 ± 12.8 | 0.01 | 2.3 ± 0.4 | 1.5 ± 0.4 | 0.01 |
| +PGE₂ | 4 | 93.2 ± 11.1 | 49.1 ± 10.6 | 0.02 | 2.5 ± 0.2 | 0.9 ± 0.2 | 0.02 |
| ST | 6 | 45.0 ± 2.8 | 29.4 ± 4.3 | 0.03 | 1.6 ± 0.2 | 1.0 ± 0.1 | 0.06 |
| +8-Br-cGMP | 6 | 80.1 ± 5.3 | 55.2 ± 6.4 | 0.002 | 2.6 ± 0.2 | 1.7 ± 0.1 | 0.01 |

Data and means ± SE for n animals.
P refers to significance of differences (paired t-test) between bromelain-treated and control tissues when $I_{sc}$ and PD responses are maximal.
PGE₂, prostaglandin E₂; theo, theophylline; 8-Br-cGMP, 8-Bromo-cGMP.

Theophylline was added to the serosal side of the tissue when $I_{SC}$ and PD values reached a plateau, indicating maximal effect of the toxin. Addition of theophylline at the end of the experiment showed similar increases in $I_{SC}$ and PD in both the bromelain-treated and PBS-treated tissue, as observed previously in LT experiments described in Example 1. This resulted in a final reduction in total $I_{SC}$ and PD of 44% (combined effect of toxin and theophylline) in tissues treated with bromelain as compared to control tissues (Table 1). This observation suggests that another mechanism for inhibiting fluid secretion exists.

2b Effect of Prostaglandin E2 (PE2) on $I_{SC}$ in bromelain treated tissue.

To observe whether the reduction in total $I_{SC}$ levels in bromelain treated tissue was because of reduced intracellular (maximal response because of ST). Similar additional increases in $I_{SC}$ and PD in both the bromelain-treated and PBS-treated tissue were noted as a result of cGMP addition, with the final total $I_{SC}$ and PD values in bromelain-treated tissues being significantly less than that of control tissues. This is shown in FIG. 4 and also in Table 1.

Significant reductions in total PD and $I_{SC}$ values was observed as in earlier experiments when tissue was treated with bromelain prior to the addition of CT or LT. The final combined $I_{SC}$ and PD values of control tissues treated with toxin followed by addition of theophylline or PE2, was significantly higher than that of bromelain pre-treated tissues.

It is hypothesised that bromelain has an additional mechanism for inhibiting fluid secretion, other than inhibiting the ability of toxin to bind to intestinal receptors. If bromelain were only to prevent the attachment of toxin to the intestinal cells, all intracellular biochemical pathways would remain unaffected. The observation that total $I_{SC}$ and PD levels in bromelain-treated tissue fail to reach the same levels as PBS-treated tissue after addition of a second messenger (ie 8-Br-cGMP, PE2 or theophylline), implies that bromelain does affect an internal signals within cells. The ability of bromelain to reduce the total $I_{SC}$ and PD changes induced by 8-Br-cGMP, implies an effect after cyclic nucleotide generation. Other molecules affect intracellular processes, for example chlorpromazine and indomethacin, however these molecules appear to be active only against submaximal doses of toxin (ST). Furthermore, these molecules have been found to be unsuitable for clinical use against diarrhoea because of undesirable side effects. Bromelain, in contrast, is effective against maximal doses of toxin and has been shown to be clinically safe.

All of the experiments described above indicate that bromelain is effective in inhibiting secretion induced by bacterial enterotoxins and also by inhibiting secretion induced by bacterial toxins combined with other secretagogues (second messengers for internal signals).

The next series of examples (Example 4 to Example 7) describe the ability of bromelain and stem bromelain to inhibit the secretion induced by second messengers alone, without the addition of bacterial toxin. Examples also demonstrate that bromelain can inhibit secretion induced by endogenous mediators of secretion (i.e. that induced by hormones or neurotransmitters or nutrients).

Example: 4 Effect of Crude Bromelain and Pure Stem Bromelain Protease on Secretion Induced by Cyclic Nucleotides Experiments were conducted in a similar manner as for those described in Examples 1 to 3, with the exception that no bacterial toxins were used in these experiments. Bromelain or stem bromelain diluted in PBS (final concentration 15 ug/ml) were added to both sides of the ileal tissue. Control tissues were treated with PBS alone. Chambers were allowed to incubate for 30 minutes and rinsed as described above. Analogues of cAMP and cGMP (8-Bromo-cAMP and 8-Bromo-cGMP; 0.2 mlM) were added to the serosal side of the tissue. These analogues induce secretion by stimulating increased levels of these cyclic nucleotides.

Figure 5:
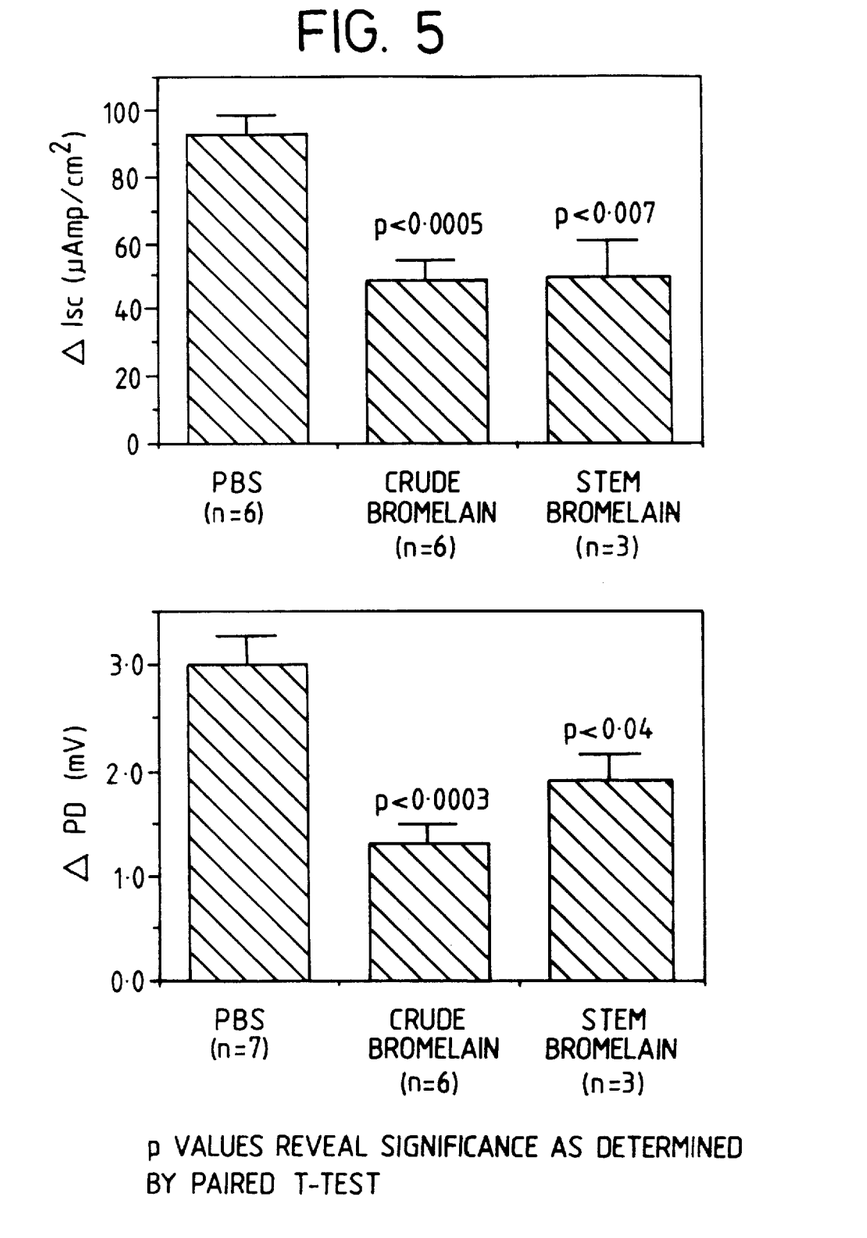
FIG. 5 shows the effect of pre-treatment of ileal tissue with PBS, stem bromelain protease and bromelain on $I_{SC}$ and PD changes caused by 8-bromo-cAMP.
Figure 6:
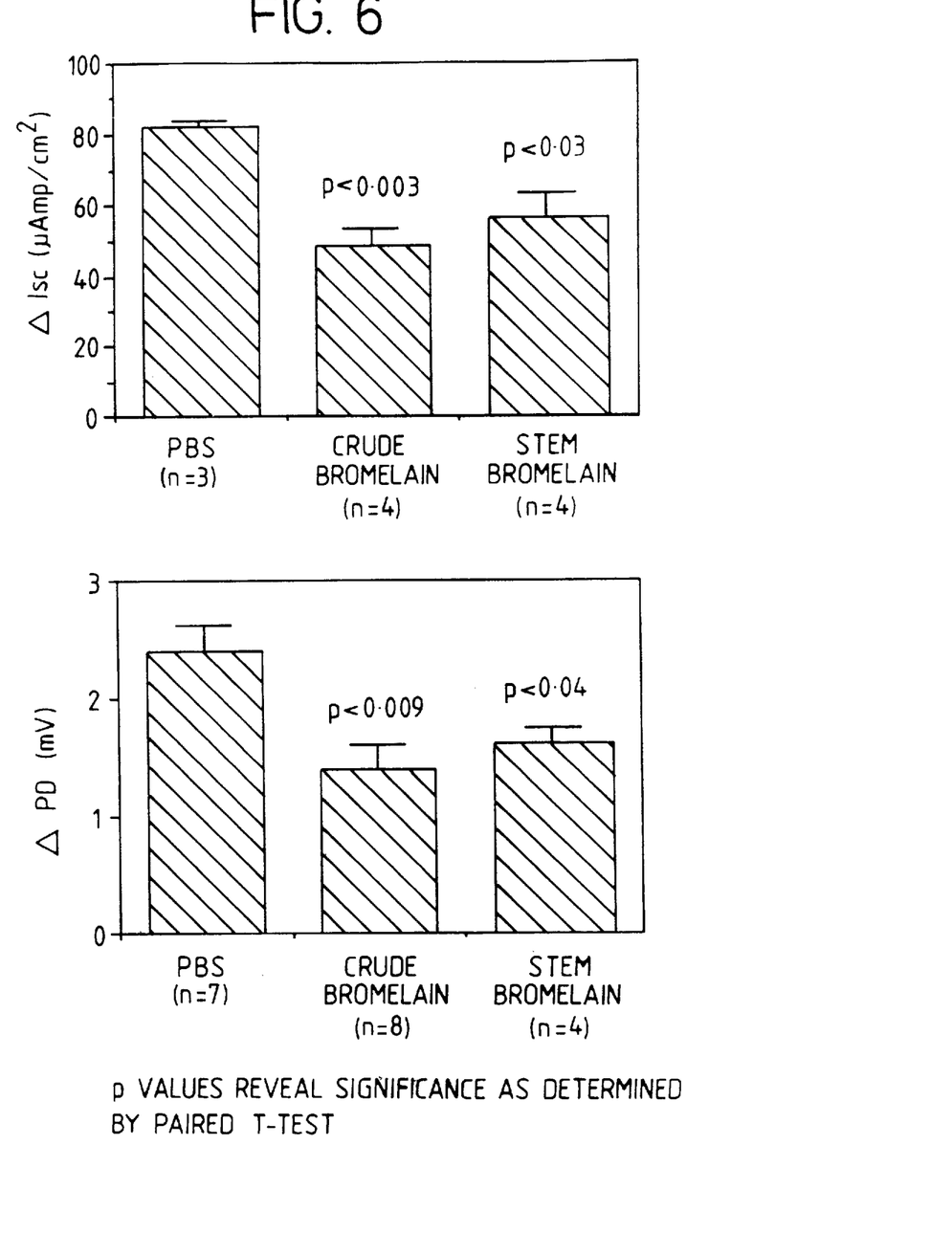
FIG. 6 shows the effect of pre-treatment of ileal tissue with PBS, stem bromelain protease and bromelain on $I_{SC}$ and PD changes caused by 8-bromo-cGMP.

FIG. 5 and FIG. 6 show the change in $I_{SC}$ and PD produced by pre-treatment of tissue with either PBS, bromelain or stem bromelain. The data show that bromelain and stem bromelain were equally effective in reducing the PD and $I_{SC}$ and therefore secretion induced by both 8-Bromo-cAMP and 8-Bromo-cGMP.

The data presented demonstrate that bromelain and stem bromelain are effective in inhibiting secretion caused by increased intracellular levels of cyclic nucleotides. This finding suggests that stem bromelain protease is responsible for the anti-diarrhoea action of bromelain.

Example 5: Effect of Bromelain on Secretion Caused by Theophylline and Prostaglandin E2

Experiments were conducted in a similar manner as for those described in Example 4. Bromelain diluted in PBS (final concentration 15 ug/ml) were added to both sides of the ileal tissue. Control tissues were treated with PBS alone. Chambers were allowed to incubate for 30 minutes and rinsed as described above. Theophylline (9 mg) or prostaglandin E2 ($1 \times 10^{-5}$M) was added to the serosal side of the tissue. These molecules stimulate secretion by action on the cAMP pathway.

Figure 7:
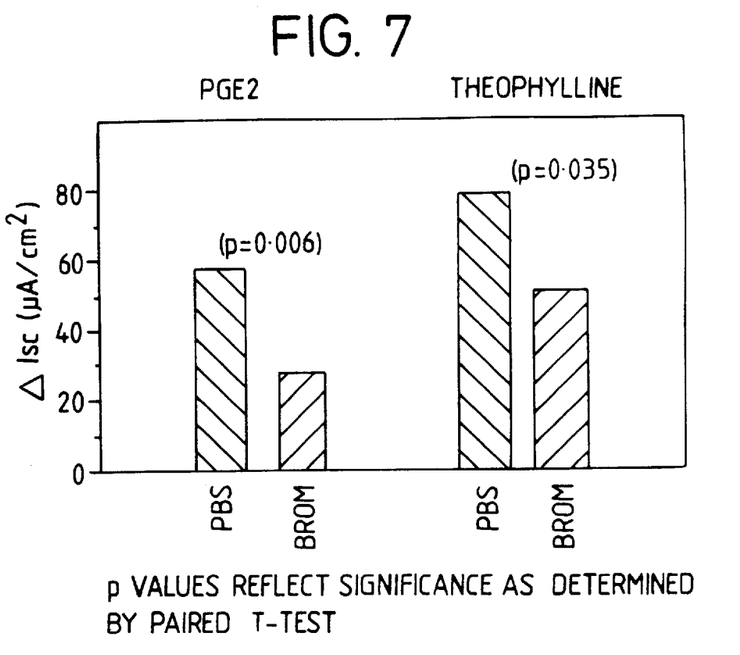
FIG. 7 shows the effect of pre-treatment of ileal tissue with PBS or bromelain on $I_{SC}$ changes caused by theophlline and PE2.

FIG. 7 shows the change in $I_{SC}$ produced by pre-treatment of tissue with either PBS or bromelain. The data show that bromelain is effective in reducing the $I_{SC}$ and therefore secretion caused by theophylline and prostaglandins.

Example 6: Effect of Bromelain on Secretion caused by a Calcium Dependent Pathway Experiments were conducted in a similar manner as for those described in Example 4. Bromelain diluted in PBS (final concentration 15 ug/ml) were added to both sides of the ileal tissue. Control tissues were treated with PBS alone. Chambers were allowed to incubate for 30 minutes and rinsed as described above. A calcium ionophore (A23187) (final concentration $5 \times 10^{-7}$M) was added to the serosal side of the tissue. Ca ionophore causes the release of calcium from stores in the endoplasmic reticulum. Increased levels of $Ca^{2+}$ in the cell stimulates secretion by action on a $Ca^{2+}$-dependent pathway.

Figure 8:
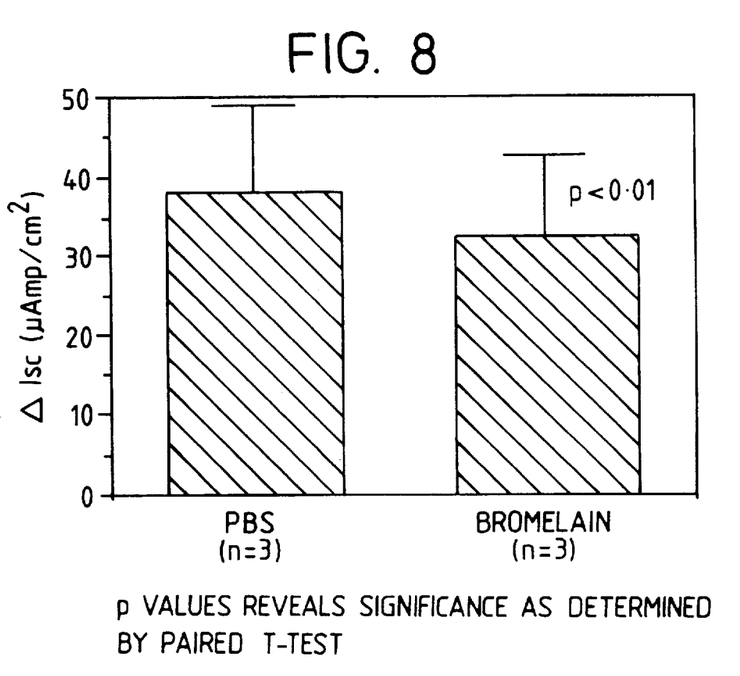
FIG. 8 shows the effect of pre-treatment of ileal tissue with PBS or bromelain on $I_{SC}$ changes caused by the calcium-ionophore A23187.

FIG. 8 shows the change in $I_{SC}$ produced by pre-treatment of tissue with either PBS or bromelain. The data show that bromelain is effective in reducing the $I_{SC}$ and therefore secretion caused by a Ca-dependent pathway.

Example 7: Effect of Crude Bromelain on Normally Function of the Intestine

7a Increase in absorption of fluid.

Experiments were conducted in a similar manner as for those described in Example 4. Bromelain diluted in PBS (final concentration 15 ug/ml) were added to both sides of the ileal tissue. Control tissues were treated with PBS alone. Chambers were allowed to incubate for 30 minutes and rinsed as described above. Tissue was continually bathed in the Ringer's solution for 90 minutes. The change in $I_{SC}$ during the 90 minutes was monitored to observe the effects of endogenous mediators of secretion (for example hormones, neurotransmitters and nutrients) and whether the tissue was absorbing or secreting.

Figure 9:
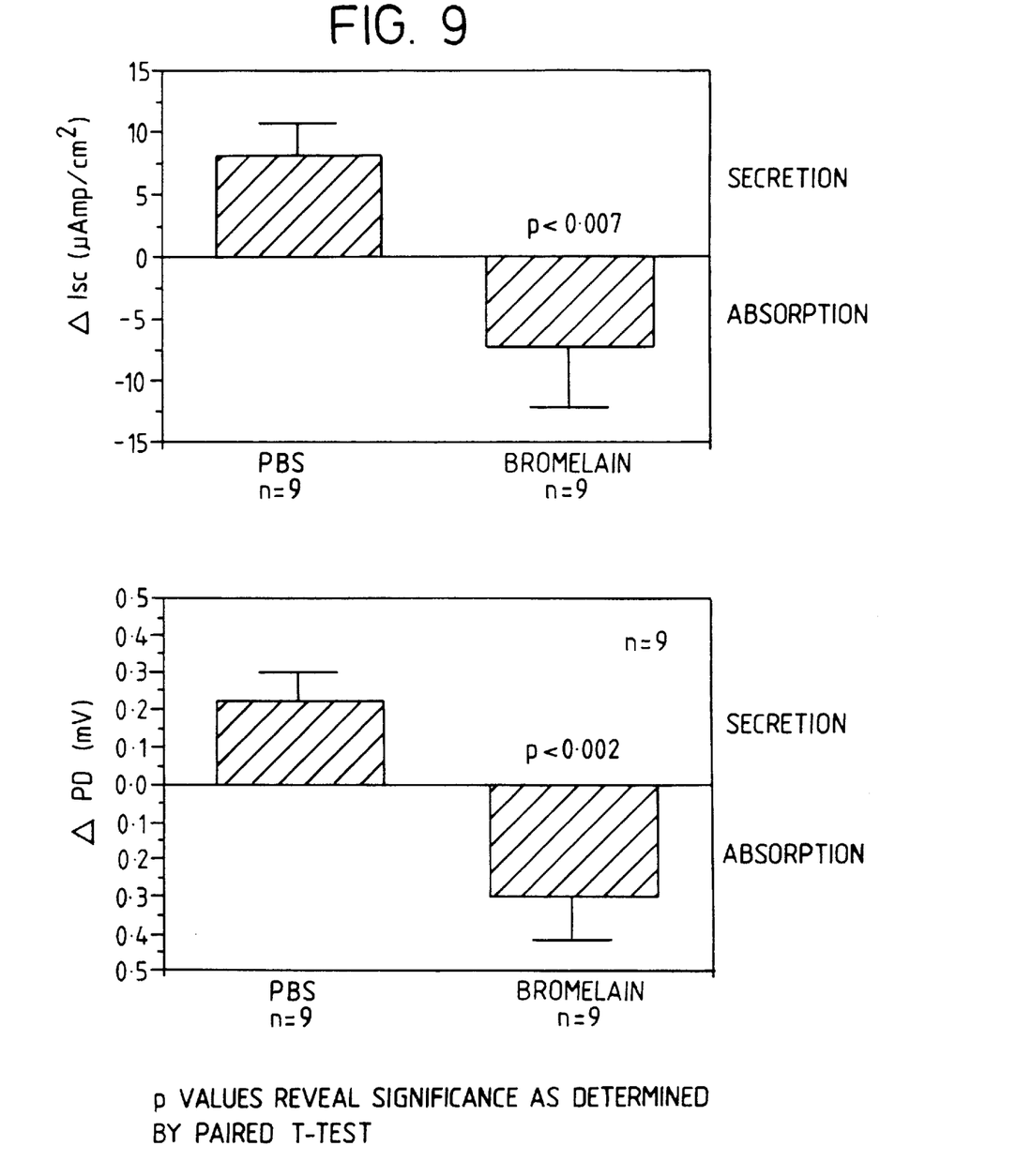
FIG. 9 shows the effect of pre-treatment of ileal tissue with PBS or bromelain on $I_{SC}$ changes caused by endogenous mediators of secretion and the ability of bromelain to stimulate absorption.

FIG. 9 shows the change in $I_{SC}$ produced by pre-treatment of tissue with either PBS or bromelain. The data show that bromelain treatment of tissue was effective in reducing the $I_{SC}$ induced by endogenous mediators of secretion and also was effective in stimulating absorption. The data demonstrate that bromelain is also effective against non-infectious diarrhoea. The fact that bromelain can inhibit secretion and enhance absorption is also a remarkable discovery in that it demonstrates that bromelain will be effective in both treating and preventing diarrhoea.

7b Increase in absorption of nutrients.

These experiments were conducted to demonstrate the effect of bromelain on other physiologically important receptors required for nutrient uptake. These studies lead to the discovery that bromelain could also enhance the absorption of nutrients.

Influx Experiments. We tested glucose influx (initial rate of unidirectional flux of glucose from the incubation medium into the epithelium) in the presence and absence of bromelain (Guandalini, S Fasano, A Albibi, F Marchesano, G Nocerino, A De Curtis, M Rualtelli, F F Pettenazzo, A & Rubino, A (1988) *Gut*, 29, 366–371) Influx of the amino acids, glutamic acid, lysine, leucine and the di-peptide, glycine-phenylalanine, was also studied.

New Zealand White rabbits were killed by chloroform inhalation. A 25 cm segment of ileum, was excised, opened along the mesenteric border and rinsed free of intestinal contents with cold Ringer's solution. Two 10 cm segments of intestine were rapidly mounted in lucite influx chambers, where four adjacent portions of the mucosal side (surface area of 0.28 cm$^2$) were exposed to the preincubation solution for 30 minutes at 37° C. and gassed with 95% of $O_2$/5% of $CO_2$. The pre-incubation solutions contained bromelain at 1 mg/ml for studies observing glucose influx, and 15 μg/ml for amino acid and dipeptide influx. Control tissues were incubated with Ringer's alone. Studies commenced when the preincubation solution was replaced with solutions of same composition, but with the presence of $C^{14}$-labelled nutrient and $H^3$-Inulin as a marker of extracellular space. Incubation in this solution was for 45–50 seconds and was stopped by quickly removing the solutions containing label and adding cold 0.3M mannitol. Each piece of exposed tissue was then punched out, gently blotted on filter paper, homogenised in 10% trichloroacetic acid and centrifuged to sediment particulate matter. Aliquots of the supernatants were assayed for radioactivity with Hpb Beckman scintillation fluid, in a Beckman LS 7500 Beta-counter. Calculations were conducted as previously described (Rubino, A Field, M & Schwachmann, H (1971), *J. Biol. Chem,* 246, 3542–3548).

Table 2 shows the effect of bromelain on nutrient influx. The data show that there is no interference with glucose and amino acid influx, indicating no adverse effects on other receptors important for nutrient uptake. The data also reveal that treatment of intestinal tissue increases the absorption of nutrients.

TABLE 2

Influence of bromelain on nutrient influx*.

| | Gly—Phe 1 mM | Leucine 1 mM | Lysine 5 mM | Glut. Ac. 1 mM | 1 mM | Glucose* 5 mM | 10 mM | 20 mM |
|---|---|---|---|---|---|---|---|---|
| Bromelain** | 0.64 ± 0.07 (n = 6) | 1.11 ± 0.09 (n = 6) | 1.3 ± 0.14 (n = 6) | 0.33 ± 0.03 (n = 6) | 0.48 ± 0.36 (n = 3) | 0.87 ± 0.19 (n = 4) | 2.19 ± 1.01 (n = 4) | 1.7 ± 1.3 (n = 2) |
| Ringer | 0.51 ± 0.04 (n = 6) | 1.04 ± 0.09 (n = 6) | 0.90 ± 0.04 (n = 6) | 0.21 ± 0.03 (n = 6) | 0.61 ± 0.35 (n = 2) | 1.01 ± 0.36 (n = 4) | 1.48 ± 0.39 (n = 4) | 1.9 ± 0.61 (n = 4) |

*Data are means ± SE for n animals. Difference between means is not statistically significant.
**Concentration of bromelain used to treat cells for amino acid influx and glucose influx experiments was 10 µg/ml and 1 mg/ml, respectively.
Gly—Phe, glycine-phenylalanine; Glut. Ac., glutamic acid.

I claim:

1. A method to treat a disease or a condition mediated by cyclic nucleotide pathways, the method comprising administering to a patient in need of such treatment an effective amount of isolated and purified stem bromelain protease of the amino acid sequence of SEQ ID NO:1, wherein said disease or condition is not diarrhoea.

2. A method of claim 1 wherein the disease or condition is selected from the group consisting of cancer, inflammation, atherosclerosis and bacterial infection.

3. A method of claim 2 wherein the bacterial infection is selected from the group consisting of diphtheria and pertussis.

* * * * *

SEQUENCE LISTING ( 1 ) GENERAL INFORMATION:

( i i i ) NUMBER OF SEQUENCES: 1

( 2 ) INFORMATION FOR SEQ ID NO: 1:

( i ) SEQUENCE CHARACTERISTICS:
( A ) LENGTH: 213 amino acids
( B ) TYPE: amino acid
( C ) STRANDEDNESS:
( D ) TOPOLOGY: unknown ( i i ) MOLECULE TYPE: protein ( x i ) SEQUENCE DESCRIPTION: SEQ ID NO: 1:

```
Ala Val Pro Gln Ser Ile Asp Trp Arg Asp Tyr Gly Ala Val Thr Ser
1               5                   10                  15

Val Lys Asn Gln Asn Pro Cys Gly Ala Cys Trp Ala Phe Ala Ala Ile
                20                  25                  30

Ala Thr Val Glu Ser Ile Tyr Lys Ile Lys Lys Gly Ile Leu Glu Pro
            35                  40                  45

Leu Ser Glu Gln Gln Val Leu Asp Cys Ala Lys Gly Tyr Gly Cys Lys
        50                  55                  60

Gly Gly Trp Glu Phe Arg Ala Phe Glu Phe Ile Ile Ser Asn Lys Gly
65                  70                  75                  80

Val Ala Ser Gly Ala Ile Tyr Pro Tyr Lys Ala Ala Lys Gly Thr Cys
                85                  90                  95

Lys Thr Asp Gly Val Pro Asn Ser Ala Tyr Ile Thr Gly Tyr Ala Arg
            100                 105                 110

Val Pro Arg Asn Asn Glu Ser Ser Met Met Tyr Ala Val Ser Lys Gln
        115                 120                 125

Pro Ile Thr Val Ala Val Ala Asp Ala Asn Ala Asn Phe Gln Tyr Tyr
        130                 135                 140
```

-continued

| Lys 145 | Ser | Gly | Val | Phe | Asn 150 | Gly | Pro | Cys | Gly | Thr 155 | Ser | Leu | Asn | His | Ala 160 |
| Val | Thr | Ala | Ile | Gly 165 | Tyr | Gly | Gln | Asp | Ser 170 | Ile | Ile | Tyr | Pro | Lys 175 | Lys |
| Trp | Gly | Ala | Lys 180 | Trp | Gly | Glu | Ala | Gly | Tyr 185 | Ile | Arg | Met | Ala 190 | Arg | Asp |
| Val | Ser | Ser 195 | Ser | Ser | Gly | Ile | Cys 200 | Gly | Ile | Ala | Ile | Asp 205 | Pro | Leu | Tyr |
| Pro | Thr 210 | Leu | Glu | Glu | | | | | | | | | | | |